United States Defensive Publication [19] (H) [11] T994,004

Shawl [43] May 6, 1980

[54] PROCESS FOR THE PREPARATION OF DIPHENYLMETHANE DICARBAMATES AND POLYMETHYLENE POLYPHENYL CARBAMATES USING SOLID ACID CATALYSTS

[76] Inventor: Edward T. Shawl, 208 Martroy La., Wallingford, Pa. 19086

[21] Appl. No.: 69,005

[22] Filed: Aug. 23, 1979

Related U.S. Application Data

[63] Continuation of Ser. No. 8,307, Feb. 1, 1979, abandoned.

[51] Int. Cl.[3] ..... C07C 125/07

[52] U.S. Cl. ..... 560/25; 560/24

[57] ABSTRACT

Diphenylmethane dicarbamates and polymethylene polyphenyl carbamate homologs and derivatives of these compounds are produced by the condensation of N-aryl carbamic acid esters, such as ethylphenylcarbamate, with formaldehyde, para-formaldehyde or trioxane in the presence of strongly acidic sulfonated aromatic ion exchange resins or perfluoroalkane sulfonic acid resins, at temperatures of from ambient to about 150° C. and optionally in the presence of an inert solvent.

10 Claims, No Sheets Drawing,

19 Pages Specification

The file of this unexamined application may be inspected and copies thereof may be purchased (849 O.G. 1221, Apr. 9, 1968).